United States Patent [19]

Solomon et al.

[11] Patent Number: 4,642,242

[45] Date of Patent: Feb. 10, 1987

[54] PERMANENTLY BONDED ANTITHROMBOGENIC POLYURETHANE SURFACE

[75] Inventors: Donald D. Solomon, Spring Valley; Charles W. McGary, Centerville; Vincent J. Pascarella, Dayton, all of Ohio

[73] Assignee: Becton, Dickinson and Company, Franklin Lakes, N.J.

[21] Appl. No.: 841,505

[22] Filed: Mar. 19, 1986

Related U.S. Application Data

[62] Division of Ser. No. 718,664, Apr. 1, 1985, Pat. No. 4,600,652.

[51] Int. Cl.[4] .......................... A01N 1/02; B05D 3/04; B05D 3/10

[52] U.S. Cl. ......................................... 427/2; 427/340; 427/352

[58] Field of Search ........................... 427/2, 340, 352

[56] References Cited

U.S. PATENT DOCUMENTS

| | | | |
|---|---|---|---|
| 3,865,615 | 2/1975 | Manly | 427/340 |
| 4,521,564 | 6/1985 | Solomon et al. | 525/54.1 |
| 4,528,343 | 7/1985 | Kira | 528/26 |

*Primary Examiner*—Joseph L. Schofer
*Assistant Examiner*—N. Sarofim
*Attorney, Agent, or Firm*—Robert P. Grindle

[57] ABSTRACT

An antithrombogenic polyurethane polymer being bound to a support substrate wherein the antithrombogenic agent is reacted through an aldehyde group with an amine functionality of a polyurethane-urea to form the covalently bonded antithrombogenic material.

7 Claims, No Drawings

PERMANENTLY BONDED ANTITHROMBOGENIC POLYURETHANE SURFACE

This is a divisional of application Ser. No. 718,664 filed Apr. 1, 1985, now U.S. Pat. No. 4,600,652.

The present invention relates to a novel antithrombogenic polyurethane polymer and process for making the same. More particularly the invention relates to a polyurethane polymer having an antithrombogenic material covalently bonded thereto so that the material is permanently affixed to the polymer and remains virtually nonleachable when the products made from the reaction product are in use.

Extensive investigations have been undertaken over many years to find materials that will be biologically and chemically stable towards body fluids. This area of research has become increasingly important with the development of various objects and articles which can be in contact with blood, such as artificial organs, vascular grafts, probes, cannulas, catheters and the like.

Artificial materials are being increasingly used as blood contact devices and may be subject to potential generation of thrombus. When blood contacts a foreign material, a complex series of events occur. These involve protein deposition, cellular adhesion and aggregation, and activation of blood coagulation schemes. Considerable research effort has been focused on this blood-material-interaction in the last twenty years. The overall objective of these investigations has been to minimize the potential for thrombus formation on the foreign materials, such as the device when introduced into the body upon contact with blood.

Early work by R. I. Leininger and R. D. Falb, U.S. Pat. No. 3,167,344, was based on binding quaternary amines to a polymer surface and subsequently ionically binding heparin thereto. In contrast, H. M. Grotta established a method in U.S. Pat. No. 3,846,353 in which heparin was complexed with a quaternary amine on a polymer surface. Both the Leininger et al. and Grotta methods have the disadvantage of being non-permanent or leachable systems. In general, ionically bound systems have limited viability due to their inherent leachability. J. Love and G. W. Holmes patented a method for the preparation of antithrombogenic surfaces in U.S. Pat. No. 3,616,935 wherein polyalkylenimines are used to irreversibly absorb the antithrombogenic compound to cellulose, cellulose esters, silicone rubber, polypropylene, polycarbonate and glass through the formation of ionic bonds. The Love et al. technique, however, was not able to overcome the deficiencies of the prior techniques, notably leaching of the antithrombogenic material rendering the system non-permanent and ineffective for long term internal use in the body.

U.S. Pat. No. 3,826,678 of A. S. Hoffman and G. Schmer relates to a covalent bonding method involving the use of "soft" hydrogel surfaces wherein radiation grafting is employed with a reactable compound selected from polymers and copolymers on an inert polymeric substrate and thereafter a biologically active compound is chemically bound to the reactable compound. "Soft" gel-like surfaces are not appropriate for devices such as catheters or other medical devices which require a "hard" Polymer surface. The "soft" hydrogel or hydrophilic surface of the Hoffman et al. patent would be subject to being stripped off catheters and in case of other blood contact devices, be devoid of the mechanical properties required. "Hard" polymers would provide the mechanical strength required in such applications.

U.S. Pat. No. 4,326,532 to Hammar discloses a layered medical article having an antithrombogenic surface wherein a natural or synthetic polymeric substrate is reacted with chitosan and the antithrombogen is then bonded to the chitosan. Hammar discloses on column 3, lines 10 to 49 that the antithrombogenic material may be ionically bonded to the chitosan or covalently bonded using boron hydrides.

In contrast to the aforementioned techniques, Larm et al. disclosed in "A New Non-Thrombogenic Surface Prepared by Selective Covalent Bonding of Heparin via A Modified Reducing Terminal Residue," Biomat., Med. Dev., Art. Org.," (283) pages 161–173 (1983) a new method for binding heparin to artificial surfaces. The procedure described involved partially degrading heparin and coupling the fragments through their reducing terminal units. Heparin was then ionically and covalently coupled to different surfaces with best results achieved using polyethylenimine containing primary, secondary and tertiary amino groups.

It would be desirable to provide a material which has excellent biological and chemical stability towards body fluids, namely blood, and which retains its antithrombogenic agent in a permanent and non-leachable fashion when in contact with blood. It would also be desirable to provide materials which, while being biocompatible, are also biofunctional, that is, materials which have biological activity in a variety of functions.

The present invention accomplishes all of these needs by use of a specific covalently bonded antithrombogenic agent to a solid support. More particularly the invention involves an antithrombogenic polyurethane polymer having (a) a support substrate; (b) a protonated amine rich polyurethane-urea bonded to said support substrate and (c) an aldehyde containing antithrombogenic agent reacted with the amine functionality of said polyurethane-urea to form a covalently bonded antithrombogenic material.

In another embodiment, the present invention involves a process for imparting antithrombogenic activity to polyurethane polymer materials which comprises (a) treating the surface of a solid support with a solution of a protonated amine rich polyurethaneurea so that the polyurethane-urea is bonded to the support substrate; (b) removing solvent from the treated substrate to form a layer of the polyurethane-urea upon the support substrate; (c) activating the amine functionality on the polyurethane-urea by use of an alkaline buffer to form free amine groups; and (d) reacting the free amine groups with an aldehyde containing antithrombogenic agent to covalently bond the antithrombogenic agent to the polyurethane-urea in the presence of a reducing agent.

The term antithrombogenic agent or material as used herein refers to any material which inhibits thrombus formation on its surface, such as by reducing platelet aggregation, dissolving fibrin, enhancing passivating protein deposition, or inhibiting one or more steps within the coagulation cascade. Illustrative antithrombogenic material may be selected from the group consisting of heparin, prostaglandins, urokinase, streptokinase, sulfated polysaccharide, albumin and mixtures thereof. The antithrombogenic material may be used in varying amounts depending on the particular material employed and ultimate desired effect. Preferred amounts have generally been found to be less than about 5% by weight of the final products and may range from about 0.2% to about 5% by weight.

The support structure used in the invention is not critical and may be selected from a wide variety of materials that are compatible with a polyurethane-urea formulation. Exemplary support surfaces may be prepared from thermoplastic polyurethanes, thermosetting polyurethanes, vinyl polymers, polyethylene, polypropylene, polycarbonates, polystyrenes, polytetrafluoroethylene, polyesters, polyvinyl chlorides and the like. The particular structures do not constitute a critical aspect of this invention other than to serve as a support substrate for the antithrombogenic agent. The supports are preferably performed into the desired shape or structure for the particular application prior to treatment according to the invention. Of significant importance is the ability of the support to bind the modified polyurethane-urea compound with the antithrombogenic agent in order to effect irreversible coupling. It has been found that any support may be used which has an average molecular weight different from the polyurethane-urea compound used to form the coupling complex and which does not dissolve in the organic solvent for the complex. This distinction is critical to enable bonding of performed supports without deformation while permitting a layer of polyurethane coupler to be bonded to the support structure. In this manner, an integral unit is formed which will not easily separate upon use.

The first step in the process of the invention involves treating the surface of the solid support with a solution of a protonated amine rich polyurethane-urea so that the polyurethane-urea material is bonded to the support substrate. The polyurethane-urea materials of the invention may be selected from a wide variety of compounds prepared by reacting a polyurethane prepolymer with a diamine.

Polyurethane-ureas are known in the art. They are generally made by chain extending the reaction product of a diisocyanate and a high molecular weight glycol (urethane prepolymer) with a diamine. Without being limited there to, one particularly preferred procedure of the present invention involves adding diamine in excess, that is from about 0.6 to 1 mole of diamine and preferably 0.75 to 1 mole for each free isocyanate group in the prepolymer to produce a polyurethane-urea with primary amine end groups. Use of ratio's below 0.6 have been found unsuitable to prepare an amine rich polyurethane-urea compound to enable sufficient reaction with the antithrombogenic agent. Ratios above about 1.0 result in the presence of nonreactive excess diamine which must be removed from the solution for adequate processing.

The urethane prepolymer can be based on a variety of diisocyanates. Suitable diisocyanates include; 1,4- cyclohexane diisocyante; dicyclohexylmethane 4,4'-diisocyanate; xylene diisocyanate; 1-isocyanate-3-isocyanatomethyl-3,5,5-trimethylcyclohexane; hexamethylene diisocyanate; 1,4-dimethylcyclohexyl diisocyanate; 2,4,4-trimethylhexamethylene diisocyanate; isocyanates such as m-phenylene diisocyanate; mixtures of 2,4-and 2,6 hexamethylene-1,5-diisocyanate; hexahydrotolylene diisocyanate (and isomers), napthylene-1,5-diisocyanate; 1-methoxyphenyl -2, 4-diisocyanate; diphenylmethane 4,4 -diisocyanate: 4,4'-biphenylene diisocyanate; 3,3 -dimethoxy - 4,4-biphenyl diisocyanate, 3,3'-dimethyl 4,4'-biphenyl diisocyanate, and 3,3'-dimethyl diphenylmethane - 4,4 diisocyanate and mixtures thereof. The aliphatic and alicyclic diisocyanates employed in the process of this invention and the products made therefrom generally exhibit good resistance to the degradative effects of ultraviolet light.

The high molecular weight glycols useful in the present invention may be a polyether diol or polyester diol and range in number average molecular weight from about 400 to about 3,000 and preferably about 500 to about 2,000. The low molecular weight glycols may also be used to prepare the prepolymer which materials may have from about 2 to 10 carbon atoms. Exemplary of the low molecular weight glycols which may be employed to prepare polyester polypols are 1,6-hexanediol, neopentyl glycol, trimethylolpropane, ethylene glycol, diethylene glycol, triethylene glycol, 1,4-butanediol, 1,4-cyclohexanediol, 1,2-propanediol, 1,3-propanediol, 1,3-butylene glycol, 1,4-cyclohexane dimethanol, 1,6,-hexanediol, and the like, and mixtures thereof.

The polyethers containing at least 2 hydroxyl groups used in accordance with the invention are also known per se and are obtained, for example, by polymerizing epoxides, such as ethylene oxide, propylene oxide, butylene oxide, tetrahydrofuran, styrene oxide or epichlorohydrin on their own, for example, in the presence of $BF_3$, or by adding the epoxides, optionally in admixture or in succession, to starter components containing reactive hydrogen atoms, such as water, alcohols, or amines, for example, ethylene glycol, 1,3- or 1,2-propylene glycol, 4,4'-dihydroxy diphenyl propane, aniline, ammonia, ethanolamine or ethylene diamine. The most preferred polyether diols are poly (tetramethylene ether) glycols.

The use of trihydric alcohols can be employed when branched polymers are desired to improve coating properties. Examples are glycerin, trimethyolpropane, adducts of trimethylolpropane or glycerin with ethylene oxide, or epsilon-caprolactone, trimethylolethane, hexanetriol -(1,2,6), butanetriol (1,2,4) and pentaerythritol.

Illustrative polyesters may contain hydroxyl groups, for example, reaction products of polyhydric alcohols reacted with divalent carboxylic acids. It is also possible to use the corresponding polycarboxylic acid anhydrides or corresponding polycarboxylic acid esters of lower alcohols or mixtures thereof, for producing the polyesters. The polycarboxylic acids may be aliphatic, cycloaliphatic, aromatic and/or heterocyclic and may optionally be substituted, for example, by halogen atoms and/or unsaturated. Examples of polycarboxylic acids of this kind include succinic acid, adipic acid, suberic acid, azelaic acid, sebacic acid, phthalic acid, phthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalic acid dimethyl ester and terephthalic acid bis-glycol ester. Examples of suitable polyhydric alcohols are ethylene glycol, 1,2-and 1,3-propylene glycol, 1,4- and 2,3-butylene glycol, 1,6-hexanediol, octanediol, neopentyl glycol, cyclohexane dimethanol (1,4-bis-hydroxy methyl cyclohexane), 2-methyl-1,3-propanediol, also diethylene glycol, triethylene glycol, tetraethylene glycol, polyethylene glycols, dipropylene glycol, polypropylene glycols, dibutylene glycol and polybutylene glycols. Polyesters of lactones, for example, ε-caprolactone or hydroxy carboxylic acids, for example, ω-hydroxycaproic acid, may also be used.

The prepolymer is prepared by heating polyols and diisocyanate with agitation in solvent under an inert atmosphere to 60°–100° C. The ratio of NCO to hydroxyl (OH) groups in the prepolymer is from 1.5 to 2:1 with a ratio of 2:1 preferred. The higher NCO to OH ratio limits the molecular weight of the prepolymer and results in higher levels of amine functionality from the diamine reaction later.

The diol molecular weight can vary from 400–3000 molecular weight. Molecular weights of about 800 to about 1500 give a combination of good film formation with adequate levels of amine functionality at the end of the reaction sequence. A catalyst may be employed but is not required. The reactants are heated for a period sufficient to react all the hydroxyl groups. The reaction time is generally 2–6 hours, however catalysts may shorten the reaction time to as little as 5 minutes. Suitable catalysts include tin salts such as dibutyltin dilaurate, stannous octoate or tertiary amines.

The prepolymer reaction is preferably carried out in solvent and in a solvent which is unreactive to NCO. Alternatively, the prepolymer may be formed neat and solvent added after the prepolymer is formed. Convenient solvents used in preparation of the prepolymer are aromatic hydrocarbons, ketones, esters, methylene chloride or tetrahydrofuran. Certain solvents have potential reactivity with amines and therefore must be evaporated prior to the addition of amines; examples of such solvents include ketones and methylene chloride.

A diamine solution is made by dissolving the amine in an appropriate solvent. Isopropanol was selected because the diamine dissolves (or disperses) readily in it and it is a secondary alcohol with a low probability of competing for available NCO groups with the amine groups. One particularly preferred final solvent mixture of toluene-isopropanol (2:1 by wt.) has the ability to solvate the highly polar polyurethane-urea.

In addition to isopropanol, methanol, ethanol, propanol, butanol, isobutanol, tert-butanol and diacetone alcohol or mixtures of alcohols may also be used.

Amines useful for this invention are: ethylene diamine, 1,3-propylene diamine, 1-4 butanediamine, 1-6 hexanediamine, 1,7-heptanediamine, 1,8-octanediamine, 1,9-nonanediamine, 1,10-decanediamine, 1,12-dodecanediamine, piperazine, phenylene diamine, tolylene diamine, hydrazine, methylene bis aniline, methylene bis 4 aminocyclohexane, isophorone diamine, 2,2,4 trimethyl-1,6-hexanediamine, menthane diamine, polyoxypropylene diamines and polyoxyethylene-diamines known as "Jeffamines" from Jefferson Chemical Company, U.S.A.

The prepolymer solution may be prepared at a concentration of 10–60%, with 30–40% being preferred (wt/wt). A solution of diamine and solvent such as isopropanol is made with a concentration of 1–30%, with 5–15% being preferred (net weight). The prepolymer is slowly added to the diamine solution with good stirring, maintaining the temperature at 30° C., in a nitrogen environment. After the reaction solution has been mixed well and the reaction is complete, a preferred optional procedure involves adding an acid slowly to the amine rich polyurethane-urea solution. A sufficient amount of acid is added to protonate the amine functionality of the amine-rich polyurethane-urea. The solution concentration is adjusted to an appropriate concentration of 5–50 weight percent, where 10–30% is preferred and 15–25% is most preferred.

The preferred acid addition technique used according to the invention prevents premature reaction of the free amine groups with carbon dioxide and other oxidizing agents present in the reaction. This is achieved by converting the amine groups into salt radicals by reaction with a protonating acid. Suitable acids include acetic acid, hydrochloric acid, phosphoric acid, formic acid, citric acid, butyric acid, toluene sulfonic acid, methane sulfonic acid and so forth. The reaction permits the amine-rich polyurethane-urea compound to be stored for long periods. It has been unexpectedly found that when this protective step was not employed, a sharp variation in results was evidenced due to variable and often relatively low amounts of antithrombogenic material bond to the polyurethane.

The choice of polyurethane-urea solvent for coating the substrate is an important factor. Many combinations of the previously listed solvents could be found useable by a coatings chemists skilled in the use of solubility parameter theory. Although the solvent mixture of toluene and isopropanol has the proper characteristics, many other combinations are useable.

Other solvents can be substituted by volatilizing the original reaction solvent and reconstituting to 5–40% by weight where 15–25% is preferred. Exemplary solvents include toluene, methanol, ethanol, propanol, isopropanol, acetonitrite, and the like. The solvent system is important to the invention but not critical or limiting.

Once prepared, the protonated polyurethane-urea is dispersed or dissolved in a solvent at the appropriate concentration of about 5% to about 40% and is contacted to form a layer upon the substrate by conventional flow or dip coating processes. Once contacting is complete, the structure is placed in a gaseous environment, preferably nitrogen, to remove the solvent. The structure is then ready for reaction with the antithrombogenic agent. Prior to reacting the protonated amine group with the antithrombogenic agent it will be necessary to activate the amine functionality on the polyurethane-urea. Activation may be conveniently performed with an alkaline buffer. The particular buffer is not critical even though it is preferred that the pH of the buffer be above about 8.0. Suitable buffers include, but are not limited to, sodium borate, sodium 5:5-diethyl-barbiturate-HCl, Clarks and Lubs solution (NaOH, KCl and $H_3BO_3$, and sodium bicarbonate.

It is essential according to the invention that the antithrombogenic agent be modified to contain a reactive aldehyde moiety which does not inhibit the bioactivity of the antithrombogenic agent when coupling is complete.

The formation of aldehyde containing agents may be achieved by conventional methods. For example when using heparin as the antithrombogenic agent, heparin may be partially depolymerized by deaminative cleavage with aldehyde inducing compounds such as sodium periodate and nitrous acid. This cleavage converts an amine bearing carbohydrate residue to a 2,5-anhydro-D-mannose residue. One preferred method to produce an aldehyde modified heparin involves the reaction of sodium heparinate with sodium periodate at a pH of between 3–7 with a preferred range of 4–5. The pH of the reaction mixture is maintained by an appropriate buffer. The reaction is carried out with the reaction vessel protected from light with constant stirring. Upon completion of the reaction, an excess of glycerin is added to neutralize the remaining unreacted periodate. The aldehyde modified heparin is then optionally dried in a nitrogen environment. The dried aldehyde modified heparin may then be simply reconstituted in an appropriate acidic buffer of pH 3.0–8.0 where 4–7 is preferred and a reducing agent such as sodium cyanoborohydride is added at weight percent of 1–40%, where 5–30% is preferred, and 5–15% most preferred. This solution is then exposed to the amine rich polyurethane-urea coated substrate. The aldehyde functional groups on the heparin are then reacted with the free amine groups to give a Schiff base formation that may be reduced to provide stable secondary amines. Exemplary reducing agents include sodium borohydride, sodium cyanoborohydride, and tetrahydrofuranborane. This reaction results in covalently bonding of the antithrombogenic agent to the polyurethane-urea.

Upon completion of the antithrombogenic coupling reaction, the surface may be washed with water to remove loosely bound or unreacted antithrombogenic agent. Washing may be optionally performed with an isotonic solution. The resulting covalently bonded heparin demonstrates high antithrombogenic activity as well as permanency and nonleachability.

The invention will be further illustrated by the following nonlimiting examples. All parts and percentages given throughout the Specification are by weight unless otherwise indicated.

EXAMPLE 1

This example illustrates the synthesis of a preferred amine rich polyurethane-urea.

29.61 g of trimethylolpropane and 215.14 g of a low molecular weight polyether polyol such as Teracol TM 650 (poly(oxytetramethylene) glycol) were added together in a mixing vessel (1.0 equivalent of each) and heated at 70° C. After equilibrating, 346.90 g (4.0 equivalents) of hydrogenated diphenyl methylene diisocyanate was added and mixing continued. 0.09 g of dibutyl tin dilaurate (0.015%) was added to the mixing solution. After at least 5 minutes of mixing the reactants were transferred to a 90° C. oven for 60 minutes. After one hour the prepolymer was removed and the percent free NCO groups was titrated and calculated. Typical values ranged from 8.0–9.5%. The prepolymer was then purged with nitrogen gas and stored.

60 g of the previously prepared prepolymer (with NCO content of 8.46%) was added to 120 g of toluene to make a 33% wt/wt solution. A diamine solution was prepared by adding 14.72 g of 1,6-hexanediamine to 80 g of isopropanol and 40 g of toluene. The diamine solution was stirred vigorously with a magnetic stir bar. The prepolymer solution was then added dropwise to the diamine solution over a two hour period. The reaction was stirred for an additional two hours. Glacial acetic acid (10 g) was then added dropwise to the reaction mixture. The resulting amine rich polyurethane-urea polymer was then dried with nitrogen gas and finally with vacuum. The amine rich polyurethane-urea polymer was then dissolved in methanol to a 20% wt/wt solution for coating.

EXAMPLE 2

This example demonstrates the preparation of an aldehyde modified heparin.

Heparin (1.0 g) was added to a sodium acetate buffer which was prepared by dissolving 0.5 g of sodium acetate in 300 ml distilled water. The pH of this solution was then adjusted to 4.5 with glacial acetic acid.

0.1 g of sodium periodate ($NaIO_4$) was added and the solution was reacted for 20 minutes in a light protected reaction vessel with constant stirring. Thereafter, 3.0 g of glycerol was added to neutralize any remaining periodate. The solution was concentrated by drying under nitrogen gas. The final solution was reconstituted to 1% wt/wt.

EXAMPLE 3

This example is illustrative of the preparation of an antithrombogenic surface according to the present invention.

An amine rich polyurethane-urea polymer of Example 1 was dissolved in methanol to a 20% wt/wt solution. A polyurethane substrate was coated with the amine-rich polyurethane-urea. After coating, the substrate was placed in nitrogen atmosphere for 60 minutes at ambient temperature. The samples were then placed in sodium borate buffer of pH 9.2, which was prepared by dissolving 57.21 g of sodium borate in 15 liters of distilled water, and stored until reaction with heparin.

The samples were then placed in a mixing vessel and aldehyde-modified heparin of Example 2 was added to a concentration of 1%. The reaction was performed in a pH 4.5 sodium acetate buffer at 50° C. Sodium cyanoborohydride (0.05 g) was added as a reducing agent. After 2 hours the samples were removed and placed in a 3M saline solution to remove any loosely bound or adsorbed heparin. Initial radiolabel assays showed that 117.2ug±3.4ug of heparin was bound per $cm^2$ of surface area. After 384 hours washing in a dynamic 3M saline solution, essentially no heparin was leached or lost. The radiolabel assay showed 112.5ug±6ug of heparin was still bound per $cm^2$. This demonstrates the permanency of the covalent bonded heparin of this invention.

EXAMPLE 4

Various length diamines can be used in the synthesis of the amine rich polyurethane-urea. This example demonstrates the use of an eight carbon diamine.

29.61 g of trimethylolpropane and 215.14 g of a low molecular weight polyether polyol such as Teracol TM 650 (poly (oxytetramethylene) glycol) were added together in a mixing vessel (1.0 equivalent of each) and heated at 70° C. Thereafter, 346.90 g (4.0 equivalents) of hydrogenated diphenyl methylene diisocyanate was added. 0.09 g of dibutyl tin dilaurate, a catalyst, (0.015%) was added to the mixing solution. After at least 5 minutes of mixing the reactants were transferred to a 90° C. oven for 60 minutes. After one hour the prepolymer was removed and the percent free -NCO groups were titrated and calculated. Typical values ranged from 8.0–9.5%. The prepolymer was then purged with nitrogen gas and stored.

15 g of the previously prepared prepolymer (with NCO content of 8.16%) was added to 30 g of toluene to make a 33% wt/wt solution. A diamine solution was prepared by adding 5.09 g of 1.8-octanediamine to 45 g of 2:1 isopropanol/toluene (by wt.) solvent mixture. The diamine solution was stirred vigorously with a magnetic stir bar. The prepolymer solution was then added dropwise to the diamine solution over a two hour period. The reaction was stirred for an additional two hours. 2.23 g of glacial acetic acid was then added dropwise. The resulting amine rich polyurethane-urea was then dried with nitrogen gas and finally with vacuum.

The amine rich polyurethane-urea polymer was then dissolved in propanol to a 15% wt/wt solution for coating.

EXAMPLE 5

This example demonstrates the effectiveness of the present invention in using longer chain diamines in the amine rich polyurethane-urea and the subsequent bonding of antithrombogenic agents.

An amine rich polyurethane-urea polymer of Example 4 was dissolved in propanol to a 15% wt/wt solution. A polyurethane substrate was coated with the amine rich polyurethane-urea. After coating, the substrate was placed in a nitrogen atmosphere for 60 minutes at ambient temperature. The samples were then placed in sodium borate buffer of pH 9.2 and stored until reaction with heparin.

The samples were then placed in a mixing vessel and aldehyde-modified -heparin, similar to that of Example 2, was added to a concentration of 1%. The reaction was performed in a pH 4.5 sodium acetate buffer at 50° C. Sodium cyanoborohydride (0.05 g) was added as a reducing agent. After 2 hours the samples were removed and placed in a 3M saline solution to remove any loosely bound or adsorbed heparin. Initial radiolabel assays showed that 113.6ug±8.2ug of heparin was bound per $cm^2$ of surface area. After 24 hours in a dynamic water wash, the radiolabel assay showed 90.7ug±4.9ug of heparin was still bound per $cm^2$. This demonstrates the permanency of the covalent bounded heparin of this invention.

The invention being thus described, it will be obvious that the same may be varied in many ways. Such variations are not to be regarded as a departure from the spirit of scope of the invention and all such modifications are intended to be included within the scope of the claims.

What is claimed is:

1. A process for imparting antithrombogenic activity to polyurethane polymer materials, which comprises:
    a. treating the surface of a solid support with a solution of a protonated amine rich polyurethane-urea so that the polyurethane-urea is bonded to the support substrate;
    b. removing solvent from the treated substrate to form a layer of the polyurethane-urea upon the support substrate;
    c. activating the amine functionality on the polyurethane-urea with an alkaline buffer to form free amine groups; and
    d. reacting the free amine groups with an aldehyde containing antithrombogenic agent to covalently bond the antithrombogenic agent to the polyurethane-urea in the presence of a reducing agent.

2. The process of claim 1 wherein the protonated amine rich polyurethane-urea is prepared from a polyurethane prepolymer and a diamine.

3. The process of claim 2 wherein the mole ratio of diamine to free isocyanate groups in the prepolymer is from about 0.6:1 to 1:1.

4. The process of claim 1 wherein the antithrombogenic agent is heparin which is reacted with an aldehyde inducing compound to form aldehyde modified heparin.

5. The process of claim 1 wherein the aldehyde inducing compound is selected from the group consisting of sodium periodate and nitrous acid.

6. The process of claim 1 wherein the alkaline buffer has a pH greater than about 8.0.

7. The process of claim 1 wherein the polyurethane polymer is selected from thermosetting polyurethane polymer and thermoplastic polyurethane polymers.

* * * * *